United States Patent
Namekawa

(10) Patent No.: US 8,637,822 B2
(45) Date of Patent: Jan. 28, 2014

(54) RADIOLOGICAL IMAGE DETECTION CASSETTE

(75) Inventor: Hiroshi Namekawa, Kawagoe (JP)

(73) Assignee: Konica Minolta Medical & Graphic, Inc. (JP)

( * ) Notice: Subject to any disclaimer, the term of this patent is extended or adjusted under 35 U.S.C. 154(b) by 0 days.

(21) Appl. No.: 13/395,506

(22) PCT Filed: Feb. 5, 2010

(86) PCT No.: PCT/JP2010/051690
§ 371 (c)(1),
(2), (4) Date: Mar. 12, 2012

(87) PCT Pub. No.: WO2011/036901
PCT Pub. Date: Mar. 31, 2011

(65) Prior Publication Data
US 2012/0168626 A1    Jul. 5, 2012

(30) Foreign Application Priority Data

Sep. 24, 2009   (JP) .................................. 2009-218604

(51) Int. Cl.
*G01J 1/00* (2006.01)
*G03B 42/04* (2006.01)

(52) U.S. Cl.
USPC ....................................... 250/336.1; 378/182

(58) Field of Classification Search
USPC ............ 250/336.1, 589, 580, 370.08, 370.09, 250/366; 378/182
See application file for complete search history.

(56) References Cited

U.S. PATENT DOCUMENTS

| | | | |
|---|---|---|---|
| 7,104,686 B2* | 9/2006 | Watanabe et al. | 378/189 |
| 2002/0085680 A1* | 7/2002 | Nakajo | 378/182 |
| 2004/0183039 A1* | 9/2004 | Iiyama | 250/589 |
| 2006/0060804 A1* | 3/2006 | Ohtsuka et al. | 250/589 |
| 2006/0227937 A1* | 10/2006 | Unger | 378/189 |

FOREIGN PATENT DOCUMENTS

| | | |
|---|---|---|
| JP | 2002-143138 A | 5/2002 |
| JP | 2005-3850 A | 1/2005 |
| JP | 2006-6424 A | 1/2006 |
| JP | 2006-212175 A | 8/2006 |
| JP | 2008-90304 A | 4/2008 |

OTHER PUBLICATIONS

International Search Report for International Application No. PCT/JP2010/051690, mailed Mar. 9, 2010, with English translation.

* cited by examiner

*Primary Examiner* — David Porta
*Assistant Examiner* — Faye Boosalis
(74) *Attorney, Agent, or Firm* — Cantor Colburn LLP

(57) ABSTRACT

A case constituting a cassette-type detector has a first lid member which closes an opening of the case arranged therein. An exterior wall hole is provided to a corner section of the first lid member. This makes it possible to detect appropriate radiological images all the time since even if an unexpected shock is applied to the corner section, the shock is absorbed by the deformation of the corner section to prevent the damage of the built-in detection unit of the cassette-type detector.

5 Claims, 4 Drawing Sheets

RADIOLOGICAL IMAGE DETECTION CASSETTE

CROSS REFERENCE TO RELATED APPLICATIONS

This is a U.S. national stage of application No. PCT/JP2010/051690, filed on 5 Feb. 2010. Priority under 35 U.S.C. §119(a) and 35 U.S.C. §365(b) is claimed from Japanese Application No. 2009-218604, filed 24 Sep. 2009, the disclosure of which are also incorporated herein by reference.

TECHNICAL FIELD

The present invention relates to a radiological image detection cassette.

BACKGROUND

Over recent years, as methods in which a subject is irradiated with radiation and radiation having been passed through the subject is detected to obtain radiological images, digital-type radiological image detection devices are being used. Such radiological image detection devices include so-called FPDs (Flat Panel Detectors).

As one example of the FPDs, there is known a detector in which on a substrate, a plurality of detection elements are two-dimensionally arranged; a phosphor (a scintillator) is irradiated with radiation having been passed through a subject; visible light emitted based on the amount of irradiated radiation is converted into a charge to be accumulated in a photoelectric conversion element; and then the charge having been accumulated in the photoelectric conversion element is read out to obtain a radiological image. Such an FPD features immediacy in which immediately after image capturing, a radiological image is obtained.

A cassette (a cassette-type FPD) is carried to a specified location to be used for image capturing of a radiological image. However, when the cassette is dropped by mistake in the middle of being carried to the specified location or struck against another object, a sudden impact is applied to the cassette in some cases. If no countermeasures are taken against this impact, the cassette may break down.

Therefor, techniques, in which the impact resistance of a cassette is taken into consideration, have been proposed. In the technique described in Patent Document 1, corner sections of an X-ray detector (hereinafter, referred to as "a cassette") are provided with caps formed of an impact resistant energy absorbing material such as nylon or polyethylene. In cases in which caps are provided for corner sections of a cassette, even when a sudden impact is applied to the corner sections of the cassette, the impact is absorbed by the caps and thereby the cassette can be prevented from breaking down.

PRIOR ART DOCUMENT

Patent Document

Patent Document 1: Unexamined Japanese Patent Application Publication No. 2008-90304

BRIEF DESCRIPTION OF THE INVENTION

Problems to be Solved by the Invention

However, as seen in the cassette described in Patent Document 1, when an impact is intended to be absorbed by caps provided in corner sections, the caps need to have thickness to some extent. Then, when such caps having thickness to some extent are provided in the corner sections, the size of the entire cassette is increased by the thicknesses of the caps.

In accordance with the standardized size of a conventional screen/film cassette, in any cassette compatible with the conventional cassette, the size of the entire cassette is limited, and thereby, when caps thick enough to absorb an impact as seen in the cassette described in Patent Document 1 are provided, the entire cassette is hard to fall in the standardized side, which is problematic.

Therefor, an object of the present invention is to provide a radiological image detection cassette in which breakdown of a cassette due to a sudden impact is inhibited.

Means to Solve the Problems

To achieve the above object, the radiological image detection cassette according to the present invention is a portable radiological image detection cassette, in which radiation having been delivered toward a subject is detected to produce radiological image data, having a detection section to output an electrical signal corresponding to incident radiation and an opening, in which a case to incorporate the detection section and a lid section to close the opening are provided, and a corner section of the lid section is provided with a hole.

Effects of the Invention

The radiological image detection cassette according to the present invention makes it possible that with a reduced size of a cassette, even when a sudden impact is applied due to dropping, the cassette can be prevented from breaking down and thereby an appropriate radiological image can be detected at all times.

PREFERRED EMBODIMENT OF THE INVENTION

Brief Description of a Cassette-Type Detector

Figure 1:
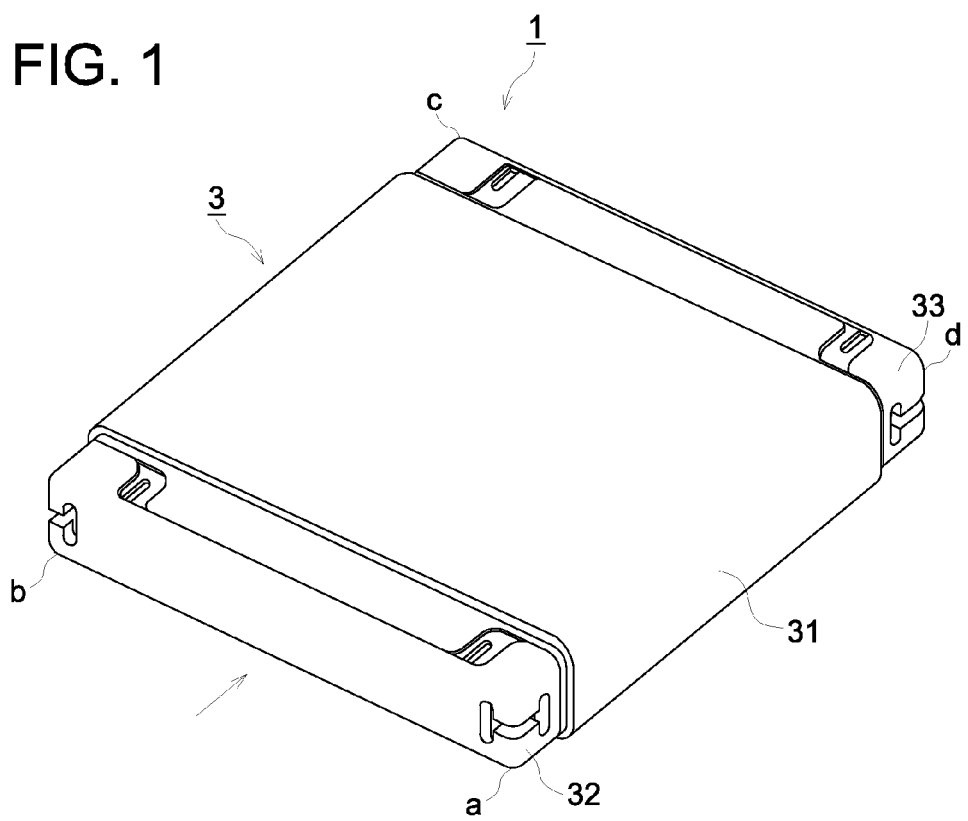
FIG. 1 is a perspective view of a cassette-type detector.

FIG. 1 is a perspective view of a cassette-type detector 1. The cassette-type detector 1, which is a radiological image detection cassette, is a cassette-type flat panel detector. The main section of the cassette-type detector 1 contains a radiation detection section 2 (refer to FIG. 5) to detect irradiated radiation to produce digital image data and a housing 3 to incorporate the radiation detection section 2. The housing 3 contains a case 31, a first lid member (a lid section) 32 to close an opening of the case 31, and a second lid member (a lid section) 33. Although not shown in FIG. 1, the first lid member 32 and the second lid member 33 are screw-fixed to the case 31.

In the present embodiment, the housing 3 is formed so that the thickness of its radiation incident direction is 15 mm. Incidentally, the thickness of the radiation incident direction of the housing 3 is at most 16 mm, which falls in the range of the size (15 mm+1 mm and 15 mm−2 mm) based on the standard (JIS Z 4905) with respect to the conventional screen/film cassette (the international standard corresponding to JIS Z 4905 is IEC 60406).

Figure 2:
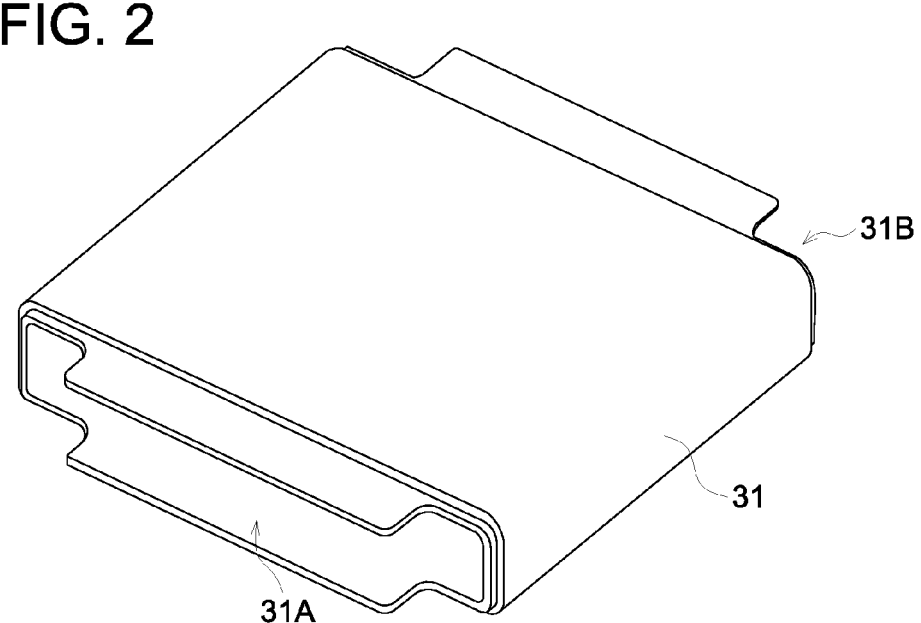
FIG. 2 is a perspective view of a case.

FIG. 2 is a perspective view of the case 31.

The case 31 is made of carbon (for example, carbon fiber reinforced plastic: CFRP), featuring reduced weight and excellent strength. Further, excellent X-ray transmittance is shown. As shown in FIG. 2, the case 31 has a hollow, cylindrical shape, being formed so as to maintain the strength of the cassette-type detector 1. On both sides of the case 31, there are openings 31A and 31B, and the opening 31A is closed by the first lid member 32 and the opening 31B is closed by the second lid member 33 (refer to FIG. 1).

The first lid member 32 and the second lid member 33 are formed of aluminum which is a metal to enhance the rigidity of the entire cassette-type detector 1 so as not to be damaged due to dropping of the cassette-type detector 1. Further, the first lid member 32 and the second lid member 33 can be formed of aluminum alloy. The cassette-type detector 1 is portable and therefore, in consideration of portability and setting properties with respect to an imaging stand such as a bucky, the first lid member 32 and the second lid member 33 are effectively formed of magnesium alloy having further reduced weight. The specific gravity of aluminum alloy is 2.7 and the specific gravity of magnesium alloy is 1.8. Therefore, magnesium alloy makes it possible that the weight of the first lid member 32 and the second lid member 33 is reduced to about ⅔, compared with the case of use of aluminum alloy. Further, magnesium alloy features more enhanced specific strength, specific rigidity, and vibration absorbability (attenuation rate) than aluminum alloy.

Figure 3:
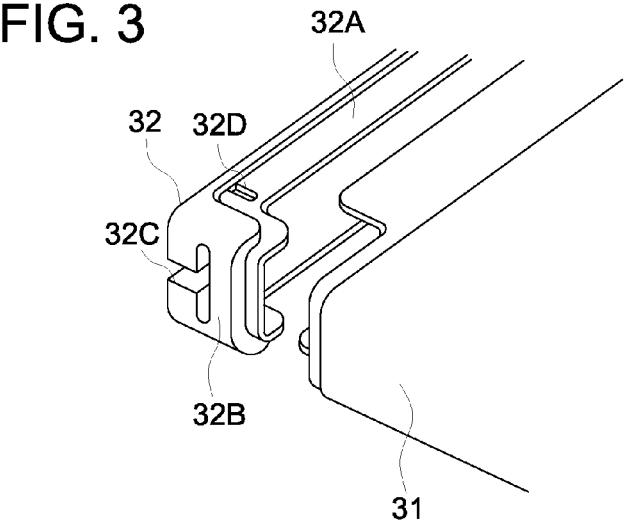
FIG. 3 is a partial perspective view showing the structure of the case and a first lid member.

FIG. 3 is a partial perspective view showing the structure of the case 31 and the first lid member 32 when viewed from an angle differing from those in FIG. 1 and FIG. 2.

The majority of the inserting section 32A in the first lid member 32 is structured so as to penetrate the interior of the case 31 when the opening 31A (refer to FIG. 2) of the case 31 is closed by the first lid member 32. On the other hand, the external wall 32B of the first lid member 32 does not penetrate the interior of the case 31 even when the opening 31A of the case 31 is closed by the first lid member 32.

Herein, the first lid member 32 and the second lid member 33 have almost the same shape. By employing the structure described in FIG. 4, the openings 31A and 31B each are closed by the first lid member 32 and the second lid member 33. Both ends of the first lid member 32 and both ends of the second lid member 33 are structured so as not to penetrate the interior of the case 31, being able to protect a carbon fiber body of the four corners of the case 31. Thereby, the carbon of the four corners of the case 31 can be protected against breakage resulting from the impact due to dropping of the cassette-type detector 1.

Figure 4:
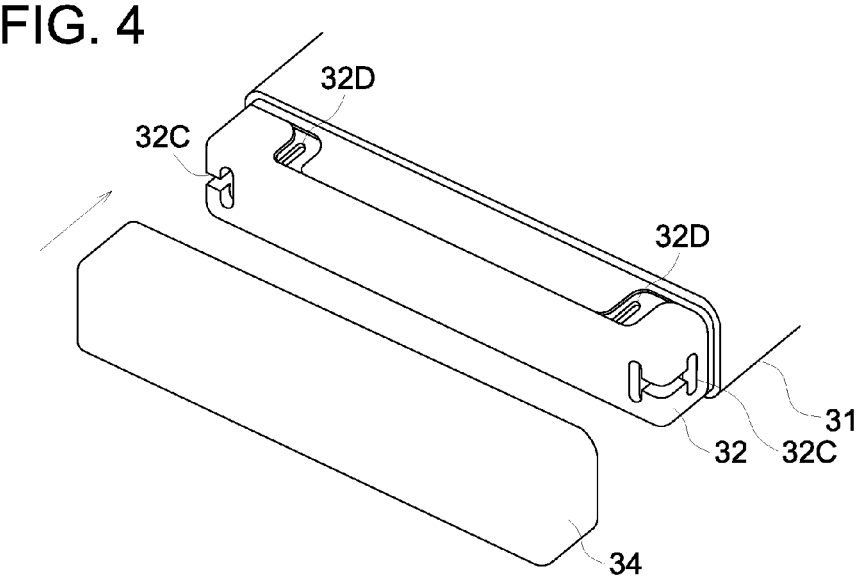
FIG. 4 is an illustration view of a protective cover mounted on the outside of the first lid member.

FIG. 4 is an illustration view of a protective cover mounted on the outside of the first lid member.

As the final form of the cassette-type detector 1, a protective cover 34 is mounted on the outside of the first lid member 32. As described later, the corner sections of the first lid member 32 are provided with an external wall hole 32C and a side wall hole 32D, and the first lid member 32 is closed by the protective cover 34 so that the user does not touch the external wall hole 32C or the side wall hole 32D when holding the cassette-type detector 1. Further, the protective cover 34 is formed of a resin for weight reduction as the entire cassette-type detector 1.

In FIG. 4, the relationship between the first lid member 32 and the protective cover 34 is merely shown. However, also on the outside of the second lid member 33 opposed to the first lid member 32, a protective cover is mounted in the same manner.

The Internal Structure of the Cassette-Type Detector

Figure 5:
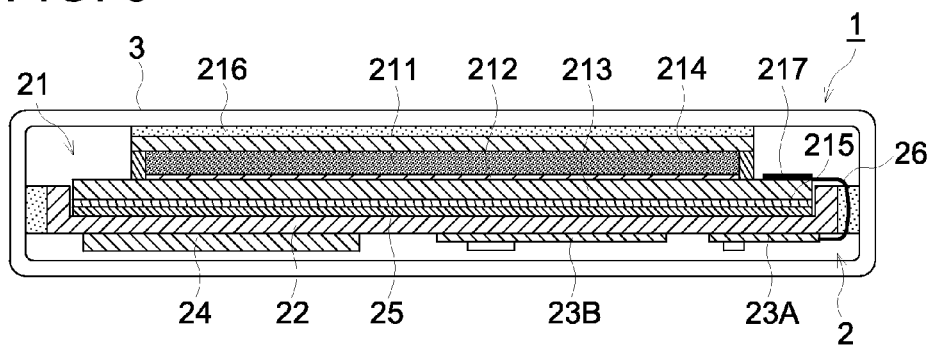
FIG. 5 is a cross-sectional view of a given portion when the cassette-type detector shown in FIG. 1 is viewed from the arrow direction of FIG. 1.

Next, the internal structure of the cassette-type detector 1 will be described. FIG. 5 is a cross-sectional view of a given portion when the cassette-type detector 1 shown in FIG. 1 is viewed from the arrow direction of FIG. 1.

As shown in FIG. 5, the radiation detection section 2 contains a detector unit 21, a base 22, and electrical components (e.g., a relay substrate 23A, a control substrate 23B, and a rechargeable battery 24). In the present embodiment, on the surface above the base 22, a detector unit 21 is placed via a shield member 25. And, on the surface below the base 22, a plurality of electrical components such as a control substrate 23B and a rechargeable battery 24 are placed.

The base 22 is flexible, which is made of a thin resin. The thickness thereof is about 1 mm, and the material is, for example, a resin in which polycarbonate and ABS are mixed.

The detector unit 21 contains a scintillator layer 211, a detection section 212, a sensor array substrate 213, an opposite substrate 214, and a buffer material 215. The fundamental structure of the detector unit 21 will be described. The detection section 212 is supported on the sensor array substrate 213 and thereon, the scintillator layer 211 is placed. Above the scintillator layer 211, the opposite substrate 214 is placed, and the scintillator layer 211 is sandwiched by the opposite substrate 214 and the sensor array substrate 213.

The scintillator layer 211 functions to convert incident radiation into light. The scintillator layer 211 incorporates, for example, a phosphor as a main component and outputs, based on incident radiation, an electromagnetic wave of a wavelength of 300 nm-800 nm, i.e., an electromagnetic wave (light) ranging from ultraviolet light to infrared light including visible light in the center.

Below the scintillator layer 211, the detection section 212 is formed. The detection section 212 converts an electromagnetic wave (light) having been output from the scintillator layer 211 into electrical energy to be accumulated and outputs an electrical signal based on the accumulated electrical energy.

The sensor array substrate 213 and the opposite substrate 214 are made of glass substrates each having a thickness of about 0.6 mm.

Below the sensor array substrate 213, a buffer material 215 is placed to reinforce the projected portions of the sensor array substrate 213 with respect to the opposite substrate 214 and to absorb the load applied to the sensor array substrate 213. Further, above the opposite substrate 214, a protective member 216 is placed to protect the opposite substrate 214.

In an end portion of the sensor array substrate 213, an electrical signal extraction section 217 is placed to extract an electrical signal having been generated in the detection section 212. The electrical signal extraction section 217 and a first relay substrate 23A are connected together by a flexible harness 26.

As the rechargeable battery 24 placed on the surface below the base 22, in the present embodiment, a lithium ion capacitor is used.

As described above, a cassette-type detector 1 as shown in FIG. 1-FIG. 5 is employed and thereby a radiological image of a subject can be detected.

External Wall Holes in the First Lid Member and the Second Lid Member

Next, a structure to inhibit the breakdown of a cassette-type detector 1 due to a sudden impact will be described.

Figure 6:
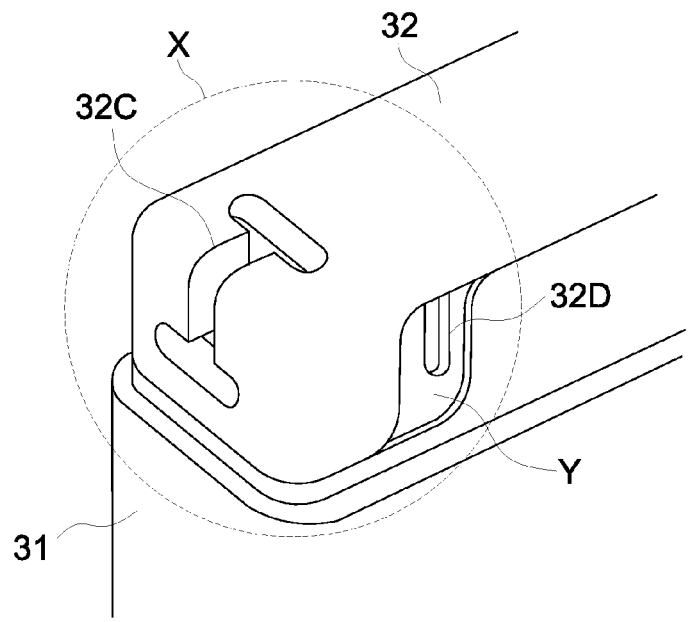
FIG. 6 is an enlarged perspective view of a corner section in the first lid member.

FIG. 6 is an enlarged perspective view of a corner section in the first lid member 32.

As shown in FIG. 6, the corner section X of the first lid member 32 is provided with a groove-shaped external wall hole (a hole) 32C, and the side wall Y of the first lid member 32 is also provided with a groove-shaped side wall hole (a hole) 32D. In FIG. 1, all of these are not show, but the corner sections a, b, c, and d, which are the four corners of the cassette-type detector 1, each are provided with an external wall hole 32C and a side wall hole 32D having the same shapes as shown in FIG. 6.

A cassette-type detector 1 is carried to a specified location to be used for image capturing of a radiological image. When the cassette-type detector 1 is dropped by mistake in the middle of being carried to the specified location or struck against another object, a sudden impact is applied to the corner section X of the first lid member 32 in some cases. However, the corner section X of the first lid member 32 is provided with an external wall hole 32C, and thereby, even when a sudden impact is applied to the corner section X of the first lid member 32, the corner section X is deformed and then the impact is absorbed by the corner section X.

Further, as shown in FIG. 6, when a side wall hole 32D is provided, the vicinity of the side wall hole 32D is also deformed to absorb an impact, and thereby the impact in the corner section X is further absorbed.

As a result, no impact is applied to the radiation detection section 2 (refer to FIG. 5) located in the interior of the cassette-type detector 1. Thereby, the cassette-type detector 1 does not break down and then an appropriate radiological image can be detected at all times.

Further, in the corner section X of the first lid member 32, anything such as an impact absorbing elastic member is not required to be placed, and thereby the size of the cassette-type detector 1 can be controlled to be the same size as in the conventional screen/film cassette. Thereby, the compatibility with the conventional cassette can be ensured, and the cassette-type detector 1 can be set in a conventional imaging stand as is to be used.

Herein, an external wall hole 32C provided for the corner section X of the first lid member 32 may have any shape as long as the shape allows the corner section X to easily deform when applied with an impact.

Figure 7:
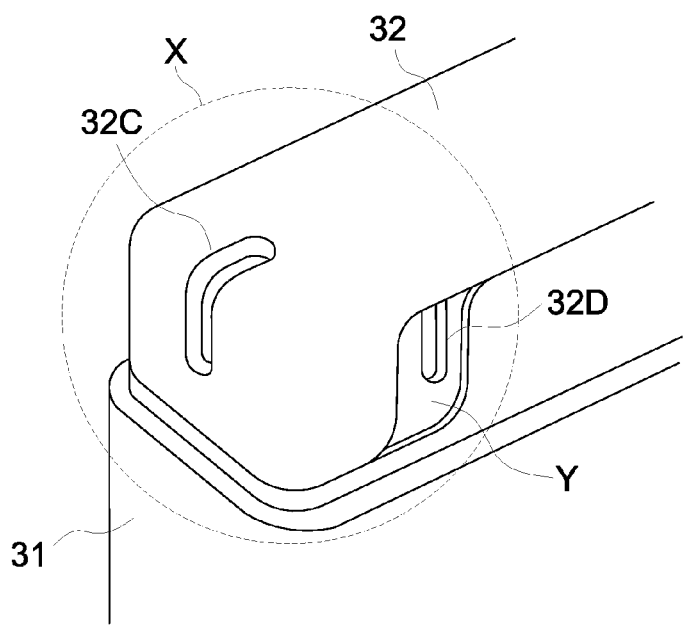
FIG. 7 is an illustration view showing a modified example of an external wall hole.
Figure 8:
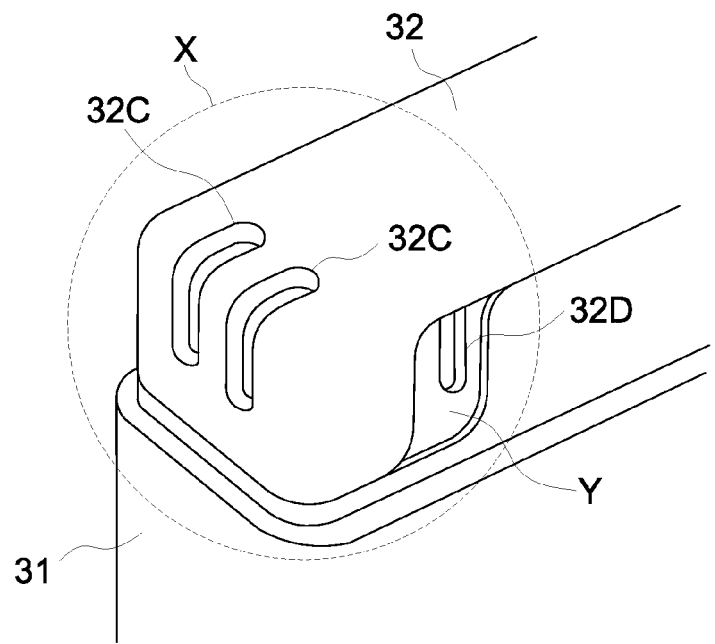
FIG. 8 is an illustration view showing a modified example of the external wall hole.
Figure 9:
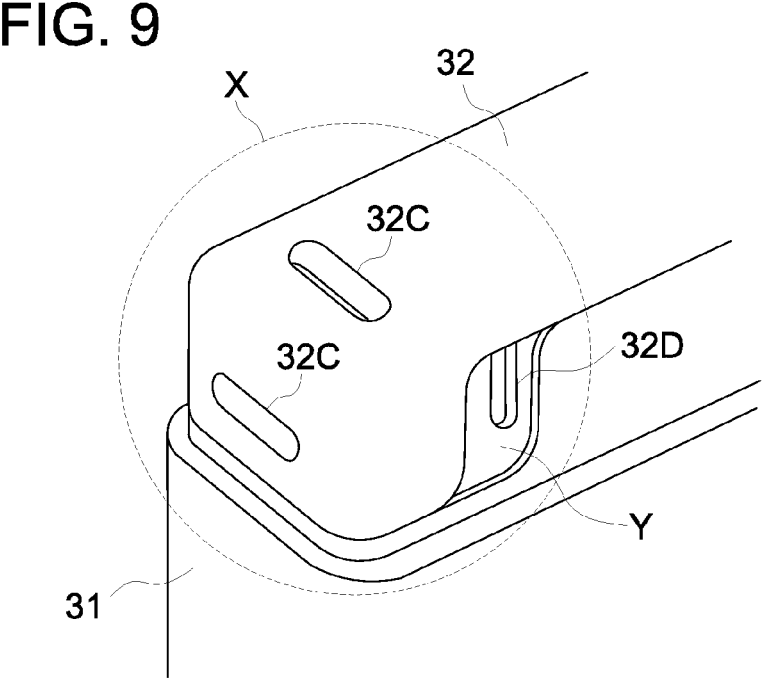
FIG. 9 is an illustration view showing a modified example of the external wall hole.

FIG. 7-FIG. 9 are illustration views each showing a modified example of the external wall hole.

For example, as shown in FIG. 7, employable is a configuration in which one straight groove-shaped external wall hole 32C is provided for the corner section X. And, as shown in FIG. 8, employable is a configuration in which 2 straight groove-shaped external wall holes 32C are provided for the corner section X. Further, as shown in FIG. 9, employable is a configuration in which 2 straight groove-shaped external wall holes 32C are provided for the corner section X in a direction differing from that shown in FIG. 8.

Further, in the embodiments shown in FIG. 6-FIG. 9, a side wall hole 32D is provided in addition to an external wall hole 32C so that the corner section X is adequately deformed by a sudden impact. However, employable is a configuration in which only an external wall hole 32C is provided or a configuration in which only a side wall hole 32D is provided.

The present invention has been described with reference to the embodiments shown in FIG. 1-FIG. 9. However, the present invention is not limited to these embodiments, and any changes and additions without departing from the gist of the present invention fall within the scope of the present invention.

In the present embodiment, a configuration, in which on the outside of a first lid member 32 and a second lid member 33, a protective cover is mounted, has been described. However, employable is a configuration in which no protective cover is mounted and then a first lid member 32 and a second lid member 33 are merely mounted in a case 31.

DESCRIPTION OF THE SYMBOLS 1 cassette-type detector
2 radiation detection section
3 housing
31 case
32 first lid member
32A inserting section
32B external wall
32C external wall hole
32D side wall hole
33 second lid member
34 protective cover

The invention claimed is:

1. A portable radiological image detection cassette which detects a radiation irradiated toward a subject to produce radiological image data, comprising:
   a detection section which outputs an electrical signal corresponding to incident radiation;
   a housing comprising:
      a case formed in a hollow and cylindrical shape and having the detection section built-in; and
      a lid section incorporated with the case to enclose the detection section and to enhance rigidity of the entire housing,
   wherein a corner section of the lid section is provided with a hole, which permits a deformation of the corner to absorb and impact applied to the housing and protect the enclosed detection section against the impact.

2. The portable radiological image detection cassette described in claim 1, wherein the lid section is formed of metal.

3. The portable radiological image detection cassette described in claim 1, wherein a protective cover is provided to hide the hole.

4. The portable radiological image detection cassette described in claim 3, wherein the lid section is made of metal and the protective cover is made of resin.

5. The portable radiological image detection cassette described in claim 1, wherein a part of the lid section is inserted into the cover.

* * * * *